(12) United States Patent
Gill

(10) Patent No.: US 10,878,961 B2
(45) Date of Patent: Dec. 29, 2020

(54) COMPUTER METHOD FOR EXPLORING DRUGS IN DISEASE

(71) Applicant: DELAWARE VALLEY OUTCOMES RESEARCH, Newark, DE (US)

(72) Inventor: James M. Gill, Newark, DE (US)

(73) Assignee: DELAWARE VALLEY OUTCOMES RESEARCH LLC, Newark, DE (US)

( * ) Notice: Subject to any disclaimer, the term of this patent is extended or adjusted under 35 U.S.C. 154(b) by 0 days.

(21) Appl. No.: 14/048,360

(22) Filed: Oct. 8, 2013

(65) Prior Publication Data

US 2014/0100881 A1    Apr. 10, 2014

Related U.S. Application Data

(60) Provisional application No. 61/710,940, filed on Oct. 8, 2012.

(51) Int. Cl.
*G16H 50/20* (2018.01)
*G06F 19/00* (2018.01)

(52) U.S. Cl.
CPC .......... *G16H 50/20* (2018.01); *G06F 19/326* (2013.01)

(58) Field of Classification Search
CPC .... G06Q 50/24; G06Q 30/02; G06Q 30/0201; G06Q 19/322; G06Q 19/326; G06F 19/3456; G16H 20/10; G16H 40/67; G16H 10/20; G16H 10/60; G16H 40/20; G16H 70/40

USPC .......................................................... 705/3
See application file for complete search history.

(56) References Cited

U.S. PATENT DOCUMENTS

| | | | |
|---|---|---|---|
| 7,509,263 B1* | 3/2009 | Fiedotin | G06F 19/324 348/516 |
| 8,301,468 B2* | 10/2012 | Lutgen | G06F 19/324 705/4 |
| 2002/0022973 A1 | 2/2002 | Sun et al. | |
| 2003/0009367 A1* | 1/2003 | Morrison | 705/9 |
| 2003/0153818 A1* | 8/2003 | Bocionek | A61B 5/411 600/300 |
| 2006/0010009 A1 | 1/2006 | Fangman | |
| 2008/0243547 A1* | 10/2008 | Brett | G06Q 10/10 705/3 |
| 2011/0313790 A1 | 12/2011 | Yao | |
| 2012/0150562 A1 | 6/2012 | Lerner | |

OTHER PUBLICATIONS

International Search Report and Written Opinion for PCT Application No. PCT/US13/63809, dated Jan. 24, 2014.

* cited by examiner

*Primary Examiner* — Hiep V Nguyen
(74) *Attorney, Agent, or Firm* — Volpe Koenig

(57) ABSTRACT

A clinical support decision marketing system is provided. A method of marketing a medication is provided. A method of evaluating and triaging a patient is provided.

2 Claims, 4 Drawing Sheets

DEPRESSION MANAGEMENT:

| PHQ-9 | ASSESS SUICIDE RISK | COMMENTS/EDUCATION | PREVIOUS/HX | SCREENING |

PATIENT'S DEPRESSION CARE IS BEING MANAGED ELSEWHERE: ○ YES ● NO  EXIT FORM

PATIENT HEALTH QUESTIONNAIRE (PHQ-9)  [PRINT QUESTIONAIRE]  PREV. EPISODE OF DEPRESSION? ● YES ○ NO

*TODAY'S SCANNED PHQ-9 CARD DATA WAS BROUGHT INTO UPDATE*  DATE OF LAST EPISODE OF DEPRESSION 8/4/06

IS THIS A NEW EPISODE OF CARE? YES  NO

INITIAL PHQ-9: 19  NO PREVIOUS SCORE
FOLLOW-UP PHQ-9: ☐

OVER THE LAST 2 WEEKS HOW OFTEN HAVE YOU BEEN BOTHERED BY ANY OF THE FOLLOWING PROBLEMS?

PREVIOUS FOLLOW-UP PHQ-9 SCORES:   NO PREVIOUS SCORES a. Little interest or pleasure in doing things...  ○0 ○1 ○2 ●3
b. Feeling down, depressed, or hopeless...  ○0 ○1 ○2 ●3
c. Trouble falling/staying asleep, sleeping too much...  ○0 ○1 ○2 ●3
d. Feeling tired or having little energy...  ○0 ○1 ○2 ●3
e. Poor appetite or overeating...  ○0 ○1 ○2 ●3
f. Feeling bad about yourself – or that you are a failure or have let ourself or your family down  ○0 ○1 ○2 ●3
g. trouble concentrating on things such as reading the newspaper or watching television  ○0 ●1 ○2 ○3

Consider Major Depression, Severe    ?

ADD ONE OF THE FOLLOWING DIAGNOSES TO THE PROBLEM LIST:

DEPRESSION, MAJOR, SNGL EPSD, SEVERE
DEPRESSION, MAJOR, RECURRENT, SEVERE

CONTINUED ON FIG. 3B    FIG. 3A

FROM FIG. 3A h. Moving or speaking so slowly that other people could have noticed. Or the opposite – being so fidgety or restless that you have been moving around a lot more than usual...  ○ 0  ○ 1  ⊙ 2  ○ 3 i. Thoughts that you would be better off dead or of hurting yourself in some way...  ○ 0  ⊙ 1  ○ 2  ○ 3

Have the above symptoms been present most of the time for 2 yrs or more with no symptom free periods for greater than 2 months?   ⊙ YES   ○ NO

TOTAL PHQ-9 SCORE: 19

PREVIOUS PHQ-9 SCORE(S): 19(08/15/2007 2:00:56 pm)
5(11/14/2006 1:58:26 pm)

ACTIVE DEPRESSION Dx's:

OTHER DEPRESSION DIAGNOSIS

GUIDELINE RECOMMENDATIONS
ANTIDEPRESSANTS ALONE OR IN A COMBINATION WITH PSYCHOLOGICAL COUNSELING VISIT OR PHONE CONTACT IN 1 WEEK

ADD MEDICATION

FOR MORE INFORMATION ON A NEW MEDICATION FOR THE TREATMENT OF DEPRESSION CLICK HERE

CLOSE

FIG. 3B

COMPUTER METHOD FOR EXPLORING DRUGS IN DISEASE

This application claims the benefit of U.S. Provisional Application No. 61/710,940, filed Oct. 8, 2012, which is incorporated herein by reference as if fully set forth.

FIELD OF INVENTION

The disclosure herein relates to a computer method for exploring drugs in disease.

BACKGROUND

A Clinical Decision Support (CDS) tool may include a pop-up form that helps physicians diagnose and treat selected medical conditions such as diabetes, depression, or high cholesterol. These forms are developed using National Guidelines of care and are appended to a patient's electronic health record (EHR). When used during an office visit the physician or a medical staff member is prompted to review current information in the EHR and/or obtain additional information from the patient about a medical condition. Based on this information, feedback is generated about whether the medical condition is being adequately controlled and if additional therapy is needed.

CDS tools improve quality of care by helping health care providers better diagnose and treat certain medical conditions. Tools can also include suicide assessment, and physician and patient education.

SUMMARY

In an embodiment, a clinical support decision marketing system is disclosed. The system includes a communication interface configured to receive clinical decision support tool data, a database containing information related to associated conditions and medications for the associated conditions, a processor for matching the clinical decision support data received with information related to associated conditions and medications for the associated conditions from the database, and subsequently identifying a marketed medication, the communication interface configured to display a link to the marketed medication in the clinical decision support tool, and a display interface configured to display information about the marketed medication.

In another embodiment, a method of marketing more cost-effective generic medications is disclosed. The method includes receiving clinical decision support tool data, identifying an associated condition from the clinical decision support tool data, identifying one or more generic medications suitable for treating the associated condition, selecting a marketed generic medication from the one or more medications suitable for treating the associated condition, displaying a link to the marketed medication in the clinical decision support tool, and displaying information about the marketed medication in the link.

In another embodiment, a method designed for lower-level health care providers to evaluate and triage a patient is disclosed. The method includes receiving clinical decision support tool data, identifying treatment options for the patient from the clinical decision support tool data, displaying a link to the treatment options in the clinical decision support tool, and displaying information about the treatment options in the link.

BRIEF DESCRIPTION OF THE DRAWINGS

A more detailed understanding may be had from the following description, given by way of example in conjunction with the accompanying drawings wherein:

FIGS. 3A and 3B illustrates a screen shot of an example Clinical Decision Support form with a marketing component.

DETAILED DESCRIPTION OF THE PREFERRED EMBODIMENTS

Figure 1:
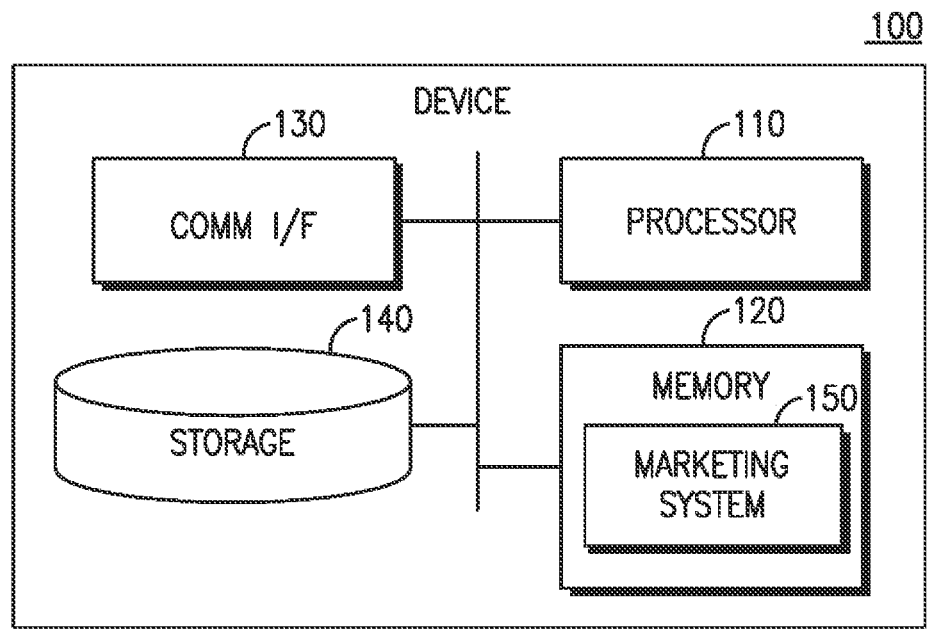
FIG. 1 illustrates an example clinical support decision marketing system according to an embodiment.

Certain terminology is used in the following description for convenience only and is not limiting. The words "a" and "one," as used in the claims and in the corresponding portions of the specification, are defined as including one or more of the referenced item unless specifically stated otherwise. The phrase "at least one" followed by a list of two or more items, such as "A, B, or C," means any individual one of A, B or C as well as any combination thereof.

Described herein is a Clinical Decision Support Marketing System, which expands on standard Clinical Decision Support tools by developing a marketing component that is embedded into the tool. This marketing pop-up component can guide a physician toward a particular appropriate medication for the patient's medical condition. The Clinical Decision Support Marketing System may be directed toward improving quality of care by increasing appropriate use of a pharmaceutical company's products. The Clinical Decision Support Marketing System may allow a pharmaceutical company to do targeted "point of care" marketing, thereby decreasing the overall cost of customer acquisition.

The Clinical Decision Support Marketing System expands on standard Clinical Decision Support (CDS) forms. A targeted marketing component is developed and added to the CDS relating to the disease focus of the CDS form. This marketing pop-up may guide the physician toward the most current treatment options available for the medical condition.

These specialized Clinical Support Tools may be inserted into a medical practices' existing Electronic Health Record. Accordingly, when a patient is seen, the appropriate CDS form automatically appears, (e.g., "pops-up"), during the visit for the physicians to use. The physicians may be prompted to current information in the EHR, and obtain additional information from the patient about the medical condition. Based on this information, the CDS form generates a recommendation to the physician about whether the medical condition is being adequately controlled and if additional therapy is needed. In addition, a marketing pop-up would appear on the form drawing a physician's attention toward a relevant treatment option.

In essence, the CDS Marketing System uses the CDS form to do one-to-one marketing to individual physicians at the time of decision, and it may reinforce to a physician the benefits of the newer/different treatment options. For example, for a patient with depression, in this enhanced marketing version of the CDS form, a pop-up may appear that directs the physician to find out about a new generation of depression drugs. Therefore, for patients who are not improving on their current medications, the physician might be prompted to consider another, newer medication.

When assessing the CDS Marketing System, it is important to remember that within a few years EHR systems may be installed in over 90% of all physicians' offices in the United States. EHRs are already used in the majority of physician's offices in many European countries. The CDS Marketing System produces a much more targeted, effective way for a pharmaceutical company to market directly to physicians. Ultimately, this may result in increased sales of a pharmaceutical company's products. The CDS Marketing System can generate revenue to pharmaceutical companies by allowing them to do targeted, point of care marketing.

In addition to pharmaceutical companies, health insurance companies may also utilize the CDS Marketing System. While pharmaceutical companies may benefit greatly from the CDS Marketing System, insurance companies and other payers may also have interest in disseminating the CDS tool. Since the CDS tool may help improve quality of care, and improved quality of primary care can lead to a reduction in expensive hospital care, the CDS tool may be attractive to healthcare payers. Also, the Clinical Decision Support Marketing System may help control healthcare costs by pointing providers to cost-effective generic drugs that may benefit a patient just as much as their brand name counterparts.

Embodiments include a clinical support decision marketing system. The system may include a communication interface configured to receive clinical decision support tool data, a database containing information related to associated conditions and medications for the associated conditions, a processor for matching the clinical decision support data received with information related to associated conditions and medications for the associated conditions from the database, and subsequently identifying a marketed medication, the communication interface configured to display a link to the marketed medication in the clinical decision support tool, and a display interface configured to display information about the marketed medication.

Clinical decision support tool data may include any information collected about the patient in the Clinical Decision Support Tool. This information may include but is not limited to information relating to the patient such as sex, age, symptoms, persistent conditions, health history, and current medications.

Information related to associated conditions in the database may include but is not limited to diseases, illnesses or conditions related to the information collected about the patient in the Clinical Decision Support Tool. Medications for the associated conditions in the database may include any medication appropriate for treatment of the associated condition.

A marketed medication is a medication selected from the medications appropriate for treatment of the associated condition in which the medication manufacturer has requested marketing through the clinical support decision marketing system. Alternatively, the marketed medication may be a medication which the insurance company has requested marketing through the clinical support decision marketing system.

The marketed medication may then be displayed in the Clinical Decision Support Tool 300 by the communication interface configured to display a link to the marketed medication. This display may include but is not limited to a pop-up box in the Clinical Decision Support Tool 300 (as shown in FIGS. 3A and 3B). The physician may click on or select the link to the marketed medication. Upon this selection, the clinical support decision marketing system may then display information about the marketed medication. Information about the marketed medication may include but is not limited to prescription information and advertising materials associated with that medication.

FIG. 1 illustrates an example clinical support decision marketing system or device 100, that may be used to implement system features described herein. The device 100 includes a processor 110, a memory device 120, a communication interface 130, and a data storage device 140. These components may be connected via a system bus in the device 100, and/or via other appropriate interfaces within the device 100.

The memory device 120 may be or include a device such as a Dynamic Random Access Memory (D-RAM), Static RAM (S-RAM), or other RAM or a flash memory. As shown in FIG. 1, the application 150, is loaded into the memory device 120.

The data storage device 140 may be or include a hard disk, a magneto-optical medium, an optical medium such as a CD-ROM, a digital versatile disk (DVDs), or Blu-Ray disc (BD), or other type of device for electronic data storage. The data storage device 140 may store instructions that define the system, and/or data that is used by the system.

The communication interface 130 may be, for example, a communications port, a wired transceiver, a wireless transceiver, and/or a network card. The communication interface may be capable of communicating using technologies such as Ethernet, fiber optics, microwave, xDSL (Digital Subscriber Line), Wireless Local Area Network (WLAN) technology, wireless cellular technology, and/or any other appropriate technology. The communication interface 130 is configured to receive clinical decision support tool data. The communication interface 130 is also configured to display a link to the marketed medication in the clinical decision support tool 300.

As shown in FIG. 1, the system 150 is loaded into the memory device 120. Although actions are described herein as being performed by the system 150, this is done for ease of description and it should be understood that these actions are actually performed by the processor 110 (in conjunction with the persistent storage device 140, network interface 130, memory 120, and/or peripheral device interface) in the device, according to instructions defined in the system or via third party server accessed by the system. Alternatively or additionally, the memory device and/or the data storage device in the device may store instructions which, when executed by the processor, cause the processor to perform any feature or any combination of features described above as performed by the system. Alternatively or additionally, the memory device and/or the data storage device in the tablet computing device may store instructions which, when executed by the processor, cause the processor to perform (in conjunction with the memory device, communication interface, data storage device, touchscreen display, and/or motion detector) any feature or any combination of features described above as performed by the system.

The device 100 shown in FIG. 1 may be, for example, an Apple iPad, or any other appropriate tablet computing device. The application 150 may run on an operating system such as iOS, Android, Linux, Windows, and/or any other appropriate operating system.

As used herein, the term "processor" broadly refers to and is not limited to a single- or multi-core central processing unit (CPU), a special purpose processor, a conventional processor, a Graphics Processing Unit (GPU), a digital signal processor (DSP), a plurality of microprocessors, one or more microprocessors in association with a DSP core, a controller, a microcontroller, one or more Application Specific Integrated Circuits (ASICs), one or more Field Programmable Gate Array (FPGA) circuits, any other type of integrated circuit (IC), a system-on-a-chip (SOC), and/or a state machine. The processor matches the clinical decision support data received with information related to associated conditions and medications for the associated conditions from the database and subsequently identifies a marketed medication.

As used to herein, the term "computer-readable medium" broadly refers to and is not limited to a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVDs, or BD, or other type of device for electronic data storage.

Although features are described herein as being performed in a tablet computing device, the features described herein may also be implemented, mutatis mutandis, on a desktop computer, a laptop computer, a netbook, a cellular phone, a personal digital assistant (PDA), or any other appropriate type of tablet computing device or data processing device.

Figure 2:
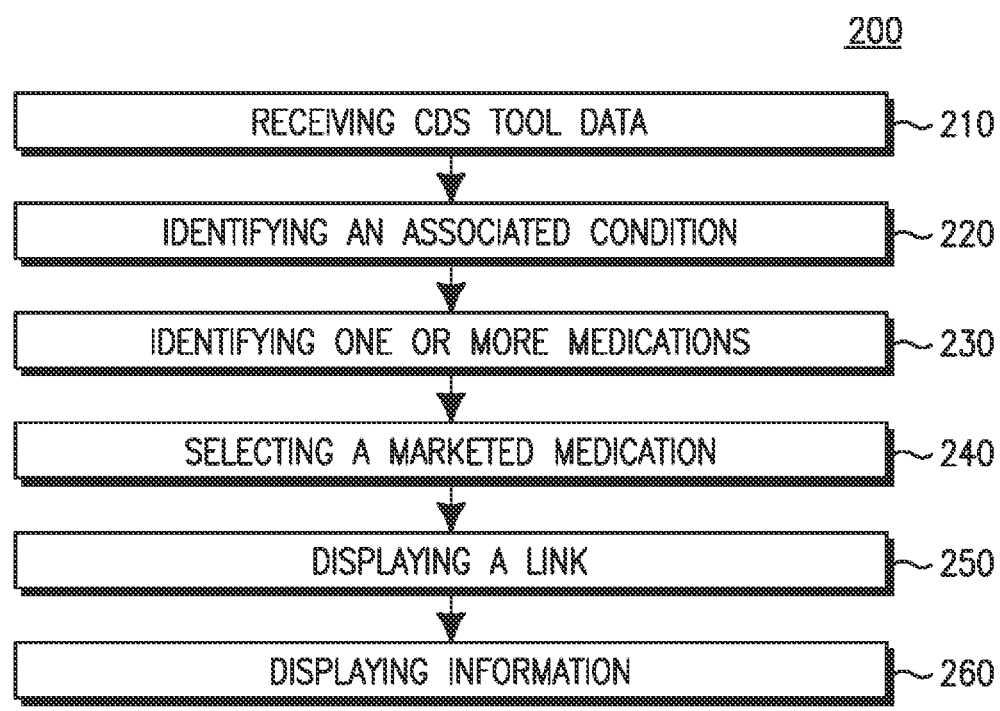
FIG. 2 illustrates an example method of marketing a medication that may be implemented on the system of FIG. 1.

Embodiments include a method of marketing a medication. Referring to FIG. 2, the method 200 may include step 210 receiving clinical decision support tool data, step 220 identifying an associated condition from the clinical decision support tool data, step 230 identifying one or more medications suitable for treating the associated condition, step 240 selecting a marketed medication from the one or more medications suitable for treating the associated condition, step 250 displaying a link to the marketed medication in the clinical decision support tool, and step 260 displaying information about the marketed medication in the link.

Receiving clinical decision support tool data at step 210 may include receiving any information collected about the patient in the Clinical Decision Support Tool 300. This information may include but is not limited to information relating to the patient such as sex, age, symptoms, persistent conditions, health history, and current medications.

Identifying an associated condition from the clinical decision support tool data at step 220 may include identifying diseases, illnesses or conditions related to the information collected about the patient in the Clinical Decision Support Tool 300.

Identifying one or more medications suitable for treating the associated condition at step 230 may include matching the identified disease, illness or condition with a medication appropriate for treating the associated condition.

Selecting a marketed medication from the one or more medications suitable for treating the associated condition at step 240 may include selecting a medication for which the manufacturer has requested marketing. Alternatively, the selected medication may be a medication which the insurance company has requested marketing.

Displaying a link to the marketed medication in the clinical decision support tool at step 250 may include a pop-up box in the clinical decision support tool 300 as shown in FIGS. 3A and 3B.

Displaying information about the marketed medication in the link at step 260 may include displaying information such as prescription information and advertising materials associated with that medication after the link in step 250 is selected.

Referring to FIGS. 3A and 3B, a screen shot is illustrated of an example of a clinical decision support tool 300 with an embedded marketing component, as shown in the lower right corner. The example in FIGS. 3A and 3B shows a Clinical Decision Support form that has been developed for Depression Management. A physician may utilize this form to help evaluation the severity of the depression. As the physician nears completion of the form attention may be drawn to the lower right corner where the CDS Marketing Component has been inserted.

Figure 4:
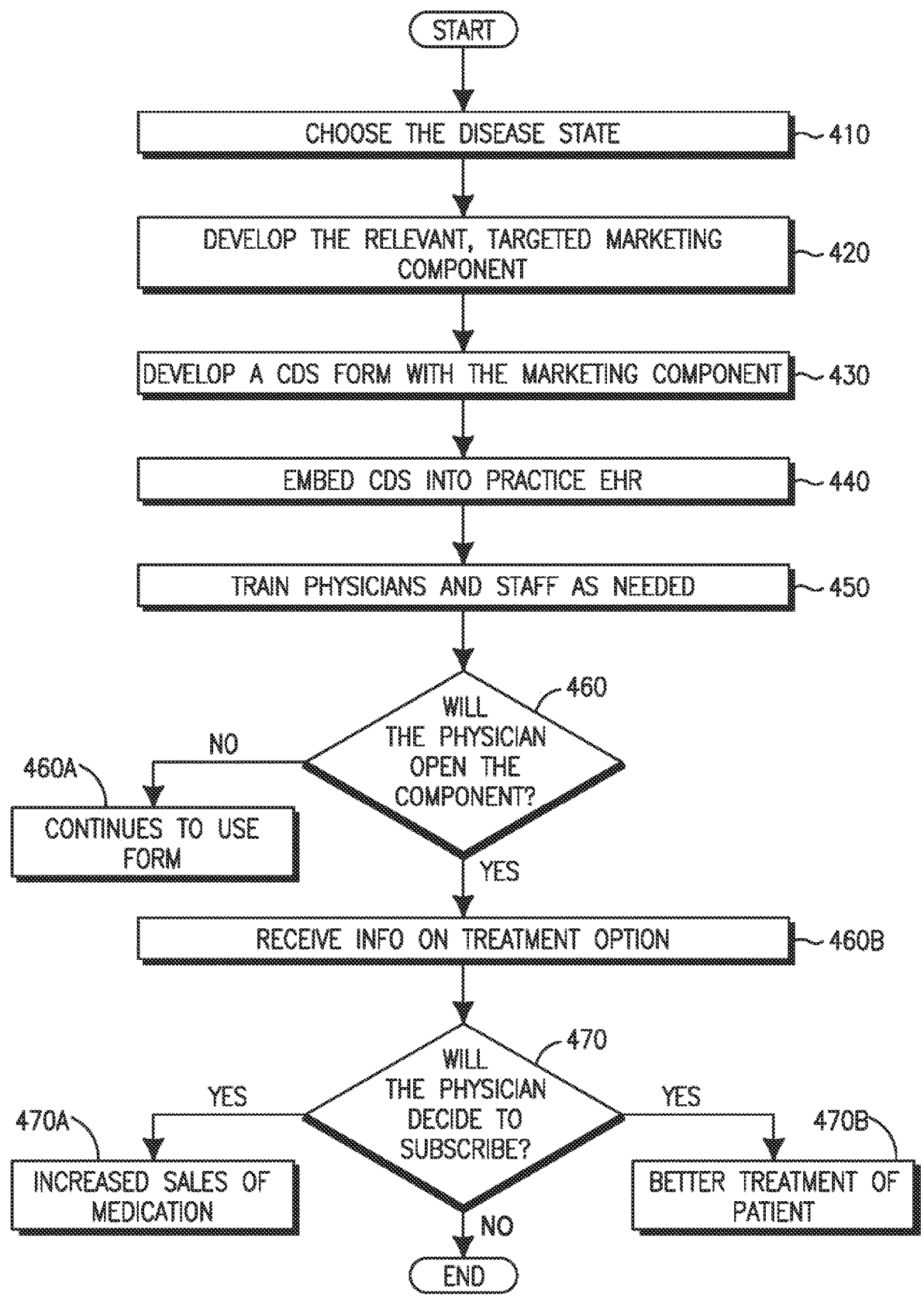
FIG. 4 is a flow diagram of an example method of a Clinical Decision Support Marketing System.

Referring to FIG. 4, a flow diagram of an example method 400 of a Clinical Decision Support (CDS) Marketing System is illustrated. In the flow diagram, a decision is made about which disease state to use for the system (i.e. diabetes, asthma). The method 400 may include step 410 choosing the disease state, step 420 developing the relevant, targeted marketing component, step 430 developing a CDS form with the Marketing Component, step 440 embedding the CDS into practice EHR, step 450 training physicians and medical staff, step 460 opening the Marketing Component by the physician, and step 470 deciding to prescribe the targeted medication. Step 460 may be bypassed by the physician, which may lead to step 460a of continuing to use the CDS form. Alternatively, step 460 may result in the physician opening the Marketing Component, which may lead to step 460b of receiving information on the treatment option. Step 470 may result in the physician prescribing the marketed medication which may lead to step 470a increasing sales of medication and step 470b receiving better treatment by the patient.

A Clinical Decision Support may be developed based on National Guidelines of care for that disease. A relevant, targeted marketing component may be developed for physicians who would be using the form. This component may primarily be a medication option that is new to the market, for which the physician may not be aware. The marketing component may be added to the CDS (see FIGS. 3A and 3B). The CDS form may be embedded in the medical practice's Electronic Health Records system. If needed, the physicians and medical staff would receive training on the use and benefits of the CDS. Therefore, when the physician or medical staff member utilized the CDS, they have the option of clicking on the point-of-care, appropriate, targeted marking component. Once the marketing component has been selected, the user will be directed to more information about that treatment option.

Embodiments may include a system and method of evaluating and triaging patients using a Clinical Decision Support tool. A medical staff member may input patient information into the CDS tool and treatment recommendations may be generated in the system. For example, in an underserved area with few physicians, a lower level health care provider may complete the CDS tool with a patient and depending on how the questions are answered, a pop-up may appear indicating that the patient either needs to see a physician or indicate treatment options not involving a physician. This may allow more care to patients and lower costs to insurance companies.

It should be noted that although for example purposes, a physician or medical staff member has been described as utilizing the tool and methods described above, any person may be able to benefit from the use. A non-limiting example may include Nurse Practitioners, Physician Assistants, Medical Assistants and any medical professional involved in health care.

Any single embodiment herein may be supplemented with one or more elements from any one or more other embodiments herein. It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A Clinical Decision Support (CDS) marketing system comprising:
    a Clinical Decision Support (CDS) system that stores information for a plurality of medications that a pharmaceutical company or insurance company wants a clinician to prescribe;
    a communication interface that is communicatively coupled to the CDS system and a patient's Electronic Health Record (EHR);
    a medication database containing information related to associated conditions and medications for the associated conditions; and
    a processor that is communicatively coupled to the communication interface and the medication database, wherein the processor is configured to:
    receive, using the communication interface, the patient's EHR,
    match the patient's EHR with information related to associated conditions and medications for the associated conditions from the medication database to identify a current treatment and a current condition,
    determine an adequacy of the current treatment based on the patient's EHR,
    on a condition that the current treatment is determined to be inadequate,
    identify a specific medication from the plurality of medications stored in the CDS system that treats the current condition,
    display, using the communication interface, a first pop-up box within the CDS marketing system, wherein the first pop-up box includes a first link to the specific medication,
    in response to a user activating with the first link, retrieve, using the communication interface,
    additional information regarding the specific medication from the CDS system,
    display the additional information and a second link within the first pop-up box, wherein the additional information includes prescription information for the specific medication and advertising materials associated with the specific medication, and
    in response to the user activating the second link, generate, using the communication interface, a prescription for the specific medication for the patient; and
    on a condition that the current treatment is determined to be adequate,
    display, using the communication interface, a second pop-up box within the CDS marketing system, wherein the second pop-up box indicates that no further treatment is required.

2. A method of providing a marketing link to a specific medication comprising:
    receiving data from a Clinical Decision Support (CDS) system that stores information for a plurality of medications that a pharmaceutical company or insurance company wants a clinician to prescribe at a communication interface that is communicatively coupled to the CDS and a patient's Electronic Health Record (EHR);
    identifying an associated condition based on the patient's EHR in the CDS system at a processor that is communicatively coupled to the communication interface and the medication database, the processor receiving the patient's EHR via the communication interface, and matching the patient's EHR with information related to associated conditions and medications for the associated conditions from the medication database to identify a current treatment and a current condition;
    determining an adequacy of the current treatment based on the patient's EHR,
    on a condition that the current treatment is determined to be inadequate,
    identifying a specific medication at the processor from the plurality of medications stored in the CDS system that treats the current condition;
    generating and displaying, using the communication interface, a first pop-up box within the CDS marketing system, wherein the first pop-up box includes a first link to the specific medication;
    in response to a user activating the first link, retrieving, using the communication interface, additional information regarding the specific medication from the CDS system, and displaying the additional information and a second link within the first pop-up box, wherein the additional information includes prescription information for the specific medication and advertising materials associated with the specific medication, and
    in response to the user activating the second link, generating, using the communication interface, a prescription for the specific medication for the patient and
    on a condition that the current treatment is determined to be adequate,
    displaying, using the communication interface, a second pop-up box within the CDS marketing system, wherein the second pop-up box indicates that no further treatment is required.

* * * * *